(12) United States Patent
Gopalakrishna et al.

(10) Patent No.: US 9,662,432 B2
(45) Date of Patent: May 30, 2017

(54) CANNULA TIP FOR AN ARTERIAL CANNULA

(71) Applicant: Carnegie Mellon University, Pittsburgh, PA (US)

(72) Inventors: Prahlad Menon Gopalakrishna, Pittsburgh, PA (US); Kerem Pekkan, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 248 days.

(21) Appl. No.: 14/404,049

(22) PCT Filed: May 28, 2013

(86) PCT No.: PCT/US2013/042940
§ 371 (c)(1),
(2) Date: Nov. 26, 2014

(87) PCT Pub. No.: WO2013/181169
PCT Pub. Date: Dec. 5, 2013

(65) Prior Publication Data
US 2015/0165110 A1 Jun. 18, 2015

Related U.S. Application Data

(60) Provisional application No. 61/689,280, filed on Jun. 1, 2012.

(51) Int. Cl.
*A61M 1/36* (2006.01)
*A61M 25/00* (2006.01)
*A61M 5/158* (2006.01)

(52) U.S. Cl.
CPC ........ *A61M 1/3659* (2014.02); *A61M 1/3666* (2013.01); *A61M 25/00* (2013.01);
(Continued)

(58) Field of Classification Search
CPC .. A61M 1/3659; A61M 1/3666; A61M 25/00; A61M 2206/20; A61M 2206/16; A61M 2025/0073
See application file for complete search history.

(56) References Cited

U.S. PATENT DOCUMENTS 5,354,288 A     10/1994  Cosgrove
5,616,137 A *    4/1997  Lindsay ............. A61M 25/007
                                                 604/264

(Continued)

OTHER PUBLICATIONS

International Search Report, mailed on Sep. 13, 2013, PCT/US2013/042940.

(Continued)

*Primary Examiner* — Bradley Osinski
(74) *Attorney, Agent, or Firm* — Tucker Arensberg, P.C.

(57) ABSTRACT

A novel arterial cannula tip includes an elongated body having an expanded four-lobe swirl inducer and a diverging diffuser. The swirl inducer presents micro-scale blood-wetting features that help to enhance the jet or core of the flow of blood sufficiently to delay the onset of turbulence and facilitate a strongly coherent blood outflow jet as it enters the cannulated artery, while the diverging diffuser reduces exit force and promotes and laminar flow which mitigates intimal vascular damage owing to high wall shear stresses at regions of jet impingement. When used in conjunction with an aortic cannula, the device facilitates neuroprotection by way of improved cerebral perfusion.

5 Claims, 6 Drawing Sheets

(52) U.S. Cl.
CPC ..... *A61M 5/158* (2013.01); *A61M 2025/0073* (2013.01); *A61M 2206/16* (2013.01); *A61M 2206/20* (2013.01)

(56) References Cited

U.S. PATENT DOCUMENTS

| | | |
|---|---|---|
| 6,059,760 A | 5/2000 | Sandmore |
| 6,254,578 B1 | 7/2001 | Grooter |
| 6,387,087 B1 | 5/2002 | Grooters |
| 2005/0038408 A1 | 2/2005 | Von Segesser |
| 2006/0253059 A1 | 11/2006 | Saunders |
| 2007/0282281 A1 | 12/2007 | Ide |

OTHER PUBLICATIONS

International Preliminary Report on Patentability, mailed on Dec. 11, 2014, PCT/US2013/042940.

Dasi et al., "Passive Flow Control of Bileaflet Mechanical Heart Valve Leakage Flow," Journal of Biomechanics, 41 (2008) pp. 1166-1173.

Menon et al., Aortic Outflow Cannula Tip Design and Orientation Impacts Cerebral Perfusion During Pediatric Cardiopulmonary Bypass Procedures, Annals of Biomedical Engineering, vol. 41, No. 12, Dec. 2013.

\* cited by examiner

CANNULA TIP FOR AN ARTERIAL CANNULA

CROSS-REFERENCE TO RELATED APPLICATIONS

This application claims the benefit of an earlier filed provisional patent application entitled, "NOVEL DESIGN AND DESIGN METHODOLOGY FOR SWIRL INDUCING AORTIC OUTFLOW CANNULA WITH A DIFFUSER TIP FOR PEDIATRIC AND NEONATAL CARDIOPULMONARY BYPASS PROCEDURES" having Ser. No. 61/689,280 which was filed on Jun. 1, 2012.

BACKGROUND OF THE INVENTION

Each year 1 in 100 children are born with a congenital heart defect, representing 40,000 children each year in the United States and 1,300,000 children worldwide with clinically significant congenital heart disease ("CHD"). Twenty five percent (25%) of pediatric CHD patients require invasive treatment to correct or palliate these defects and therefore undergo complex biventricular and univentricular repairs. These repairs involve cardiopulmonary bypass ("CPB") procedures during surgery, as well as circulatory support in the pre or post operative periods. A prolonged CPB can potentially lead to neurological complications and developmental defects in up to 50% of these young patients i.e. infants and children from 2 to 25 kg with congenital or acquired cardiovascular disease.

During CPB, tiny arterial cannulae (2-3 mm inner diameter), with micro-scale blood-wetting features transport relatively large blood volumes (0.3 to 1.0 L/min) resulting in high blood flow velocities. These severe flow conditions are likely to result in platelet activation, release of pro-inflammatory cytokines, and further result in vascular and blood damage. The cannulae are required to provide high blood volume flow rates during neonatal and pediatric cardiopulmonary bypass procedures, resulting in high velocity jet flows. These severe flow conditions initiate platelet activation, release inflammatory cytokines, and further result in vascular and blood damage. Through the design of internal flow control features and a modified cannula outflow tip, it has been made possible to result in outflow jets with low exit force at high flow rates produced with low driving pressure drops, having minimal jet wake blood damage.

Recent investigations have indicated the high hemolytic risk of standard cannulae used in the setting of neonatal CPB surgery and post intervention recovery has been reported to remain suboptimal. Common arterial cannulation sites are located at the aorta, femoral, axillary or subclavian (with or without a side graft), external iliac, and innominate artery. Arterial perfusion by cannulation of the ascending aorta is regarded as an important advance in cardiovascular surgery and is the focus of the present invention since the technique eliminates the issues of retrograde aortic perfusion and the need for a second incision for femoral cannulation during CPB. The aortic cannula must ideally be placed high up in the ascending aorta (as discussed in R. Garcia-Rinaldi, et al., "Simplified aortic cannulation," Ann Thorac Surg, vol. 36, pp. 226-7, August 1983) but improper technique can occasionally result in profuse bleeding as a result of improper cannula placement. To date, CPB has been studied in regard to clinical stroke-risk (see D. B. Andropoulos, et al., "Neuroprotection in Pediatric Cardiac Surgery: What is On the Horizon?," Prog Pediatr Cardiol, vol. 29, pp. 113-122, Aug. 1, 2010), but there have been few reported studies deriving cannula design and device use strategy from fluid dynamics associated with arterial cannulation (see T. A. Kaufmann, et al., "Flow distribution during cardiopulmonary bypass in dependency on the outflow cannula positioning," Artif Organs, vol. 33, pp. 988-92, November 2009; T. A. Kaufmann, et al., "The impact of aortic/subclavian outflow cannulation for cardiopulmonary bypass and cardiac support: a computational fluid dynamics study," Artif Organs, vol. 33, pp. 727-32, September 2009; Y. Tokuda, et al., "Three-dimensional numerical simulation of blood flow in the aortic arch during cardiopulmonary bypass," Eur J Cardiothoracic Surg, vol. 33, pp. 164-7, February 2008; A. F. Osorio, et al., "Computational fluid dynamics analysis of surgical adjustment of left ventricular assist device implantation to minimise stroke risk," Comput Methods Biomech Biomed Engin, vol. 21, p. 21, Dec. 21, 2011), all underscoring the association of biomechanical risks with aortic cannulation. Despite these risks, outflow cannula design and cannulation methods have received little attention compared to the effort expended to assure the safety and efficacy of the mechanical circulatory support blood pumps. There is a definitive need for engineering small yet hemodynamically efficient arterial outflow cannulae that can provide high blood volume flow rates but with low exit force and outflow velocity, for use in extracorporeal circulation during neonatal CPB procedures, while minimizing recognized biomechanical risks related to infection, bleeding, hemolysis and thromboembolism during mechanical circulatory support.

Unlike adult CPB perfusion cannulae (U.S. Pat. No. 5,354,288 to Cosgrove, and U.S. Pat. No. 6,387,087 to Grooters, for example) where outflow is designed to have low velocity jets that prevent dislodgement of atherosclerotic plaque with adherent blood thrombi that can potentially cause thromboembolism, the design goal for the neonatal and pediatric population is quite different. In order to assess desirable jet wake hemodynamics in small cannulae, the jet's potential core length, resistance to outflow, and normalized index of hemoylsis as major parameters to designs so as to provide high blood volume flow rates but with low exit force and outflow velocity from far smaller cannula inner diameters that those used in adults—the latter being a requirement for minimizing disruption of the child's artery during cannulation. The focus of cannula design today and the goal of this invention are therefore to minimize risk of vascular injury and risks of biomechanical origin as well as to simultaneously improve outflow rate versus driving pressure drop perfusion characteristics, which become increasingly unfavorable at reduced outflow diameters, in the case of conventional end-hole type standard cannula configurations evidenced by the prior art. In the case of the specific application aortic cannulation, the present invention may additionally improve perfusion to the head-neck vessels of the aortic arch and therefore improve cerebral perfusion, mitigating neurological complications commonly reported (neurological morbidity is as high as 30% in infants and children) in conjunction with CPB in young patients. See Fallon, et al., "Incidence of neurological complications of surgery for congenital heart disease," Arch Dis Child, vol. 72, pp. 418-22, May 1995 and H. L. Pua and B. Bissonnette, "Cerebral physiology in paediatric cardiopulmonary bypass," Can J Anaesth, vol. 45, pp. 960-78, October 1998.

BRIEF SUMMARY OF THE INVENTION

The present invention relates generally to arterial cannulae and aorta cannulae. The prior art discloses the use of small diameter cannulae for minimizing disruption to the neonatal or pediatric arteries, used to return oxygenated blood from the heart-lung machine back to the arterial circulation during CPB. The present invention is the result of a novel design approach based on the paradigm of controlling the development of fluid jets in cannula tip geometries. High performance computing computational fluid dynamics ("CFD"), particle image velocimetry ("PIV"), and flow visualization techniques in a proprietary cuboidal cannula jet testing rig are used as a design tools to compare internal hemodynamics in the early jet region of a conventional tubular cannula device having a standard end-hole, against several embodiments of the proposed novel arterial cannula design which is an elongated tube with an expanded multi-lobe swirl inducer chamber and a diffuser cone end.

This invention further relates to a hemodynamically superior arterial cannula tip designed to delay onset of turbulence in the cannula exit flow wake, while simultaneously reducing exit force of the flow, for minimizing risk of internal vascular injury, improving outflow rate versus driving pressure drop perfusion characteristics and further improving cerebral perfusion, in the case of its application to aortic cannulation. The invention encompasses a method of delivering blood to an artery using a swirl-inducing cannula having a diverging diffuser during cardiopulmonary bypass surgery, which has been specifically tailored to the requirements of neonatal and pediatric procedures.

For specific application to neonatal and pediatric CPB perfusion, and especially in the case of aortic perfusion, design considerations include a small inner diameter of a cannula to minimize disruption of the arterial flow, an expanded multi-lobe swirl inducer responsible for reducing the wall shear stress experienced by the blood in the cannula and also simultaneously improving vorticity of the coherent flow core in order to propel flow forward in a manner delaying the Reynolds number ("Re") for onset of turbulence in the flow, and finally a diverging diffuser that improves pressure-drop versus flow-rate characteristics and reduces outflow jet exit force (and outflow velocity) while simultaneously facilitating improved cerebral perfusion by mitigating backflow from the head-neck vessels of the aortic arch. The diverging diffuser tip is axis-symmetric and in one embodiment linearly increases the diameter of the cannula until the outflow and in another embodiment may non-linearly increase the diameter of the cannula until the outflow tip.

The swirl inducer design has potential applicability to adult CPB perfusion and as an attachment to existing cannula tips for purposes of improved flow hemodynamics, perfusion characteristics, as well as insertion orientation control. In an ideal use case or mode of operation, the blood flow (typically Re 650 to 3000) exiting the cannula's diffuser along the direction of the transverse aortic arch, heading towards the curvature of the descending aorta, in a manner that mitigates direct flow impingement on the walls of the transverse aortic arch or the head-and-neck vessel branches, therefore, minimizing stroke risk due to transport of dislodged thrombi from the mechanical circulatory support systems into the head-neck vessels.

DETAILED DESCRIPTION

Figure 1:
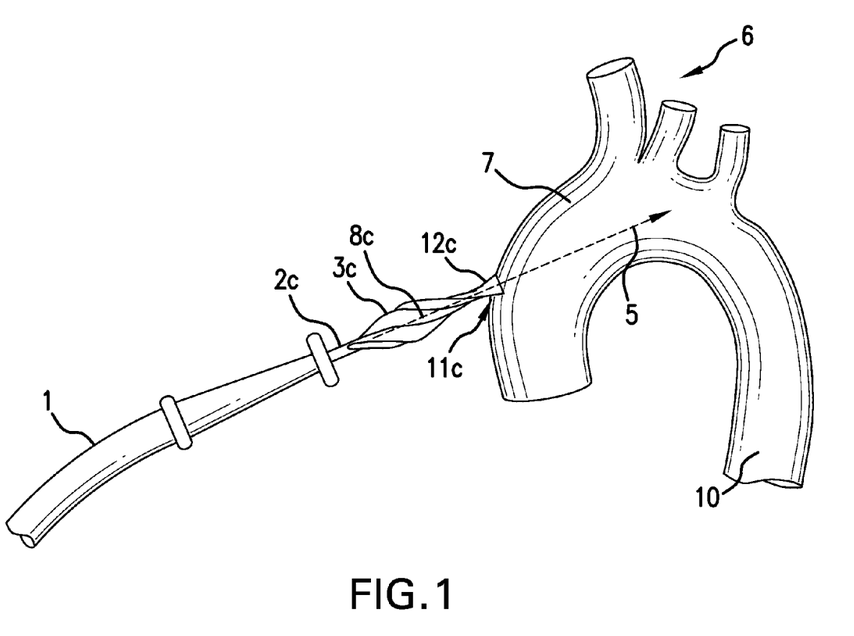
FIG. 1 illustrates a frontal view of a cannula having a cannula tip inserted into the ascending aorta. The overall size of the device and the relative size of the aorta may vary depending upon the rated diameter and specific design parameters of the cannula tip.
Figure 2:
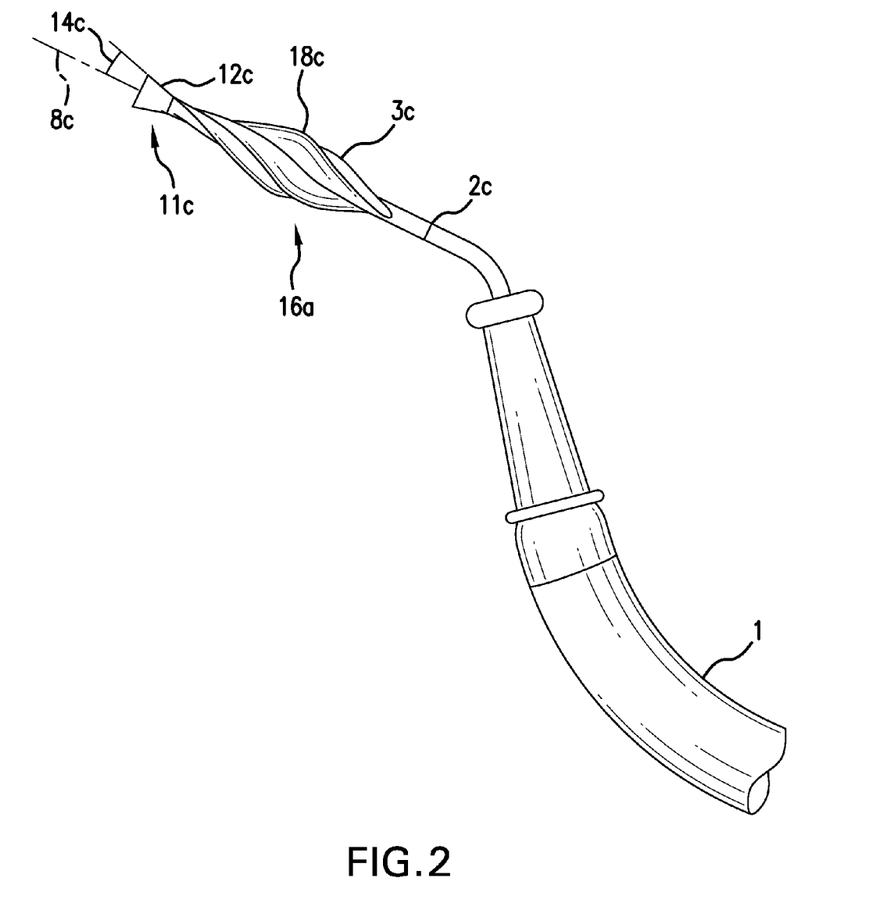
FIG. 2 illustrates an enlarged view of a cannula including an embodiment of a cannula tip.

Cannula of the type described herein directs the flow of blood from blood pumping apparatus, which is known in the art, so that it exits the cannula tip along a particular artery or in the case of an aortic artery, in a predetermined direction 5 along the transverse aortic arch 7 heading towards the curvature of the descending aorta, as may be seen by referring to FIG. 1 in conjunction with FIG. 2.

It is recognized to be advantageous to have the blood flow enter the aorta in a manner that mitigates high wall shear stress owing to harsh jet impingement on the walls of the transverse aortic arch or the head-and-neck vessel branches which may lead to intimal vascular damage, while also minimizing stroke risk due to dislodged thrombi from the mechanical circulatory support systems. It is also understood that cerebral perfusion can be improved in the aortic arch by virtue of the diffuser tip of the invention which lowers the velocity of the outflow cannula jet, averting likely backflow at the head-neck vessels of the aortic arch owing to the Venturi Effect, and therefore reducing likelihood of neurological complications associated with CPB which has been reported to be widely prevalent in the pediatric/neonatal population. Despite advances in surgical techniques, leading to decreased morbidity after repair of complex congenital cardiac conditions, neurologic morbidity is still significant. Given that the incidence of neurological morbidity is as high as 30% in infants and children undergoing CPB, in sharp contrast with 2-5% among adults, the issue of arterial perfusion deserves attention in young patients.

The invention disclosed herein presents three embodiments which attain these objectives. While some of these embodiments are discussed from the standpoint of the special case of aortic insertion, it is to be understood that they are applicable to the more general case of insertion into other arterial vessels as well.

Referring to FIGS. 1 and 2, FIG. 1 discloses a cannula tip 3c in the configuration of the third embodiment to be discussed in greater detail below, for purposes of illustration and ease of viewing. The cannula tip 3c has been partially inserted into an artery, and for purposes of this illustration, the artery is illustrated as an aorta 6. It is to be understood that any of the three embodiments discussed herein can be used in the manner of the cannula tip 3c illustrated in FIG. 1. The diffuser tip is a flexible embodiment which can be introduced into the aorta through minimal arterial disruption the size of only for the neck of the diffuser tip.

First Embodiment

Figure 3:
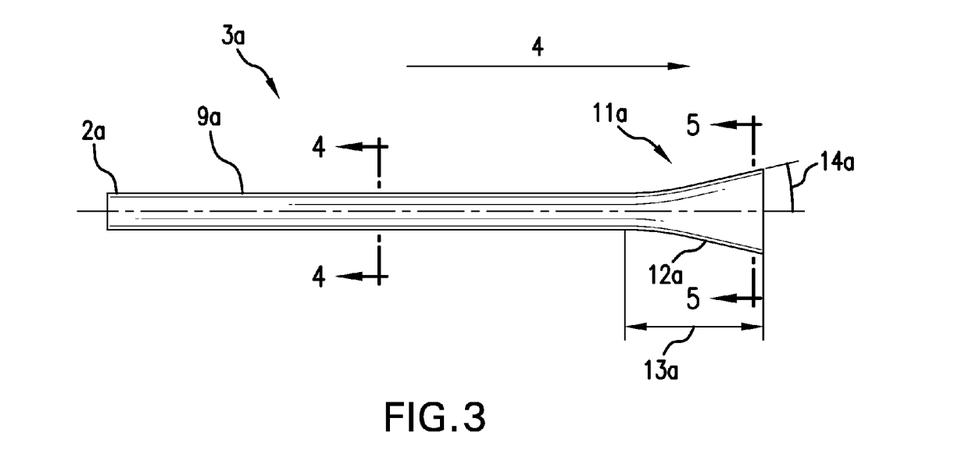
FIG. 3 illustrates an embodiment of a cannula tip showing an embodiment of the diverging diffuser type of outlet.

Referring now to FIG. 3, a cannula tip 3a is illustrated. As noted above, it should be understood that this first embodiment and the second embodiments as well, can be used in the manner illustrated by FIG. 1.

Blood is able to enter inlet 2a and flow along longitudinal axis 8a in downstream direction 4 from inlet 2a, through cannula tip body 9a and cannula tip 3a and out of diverging portion 11a, as will be discussed in greater detail. As the blood flow exits cannula tip 3a, it continues to flow in a direction 5 (direction 5 is illustrated in FIG. 1). This orientation will take the flow in the direction of descending aorta 10 and away from aortic arch 7, an important feature which will be discussed in greater detail below.

Figure 4:
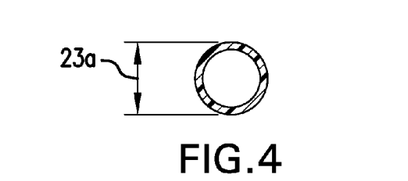
FIG. 4 illustrates a sectional view taken through section 4-4 of FIG. 3.
Figure 5:
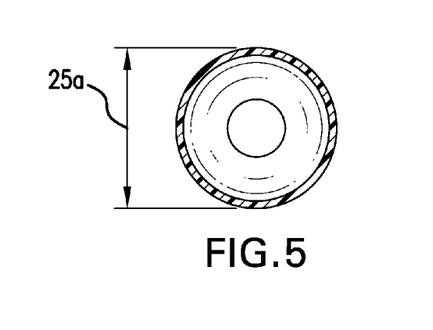
FIG. 5 illustrates a sectional view taken through section 5-5 of FIG. 3.

Still referring to FIG. 3, cannula tip 3a has an approximately cylindrical cannula tip body 9a and has a cross sectional area depicted in FIG. 4 as cylindrical. Cannula tip body 9a has inlet 2a which has first diameter 23a and a diverging portion 11a which has a larger circular cross sectional area having a second predetermined diameter 25a as depicted in FIG. 5. The surface 12a of diverging portion 11a makes an angle 14 with the longitudinal axis 8a of cannula tip 3a. In an embodiment angle 14 is 7 degrees.

As blood passes through the cannula tip body 9a, it is diffused through diverging portion 11a and its larger cross sectional area having second predetermined diameter 25a. Diverging portion 11a is illustrated as having a predetermined length 13a as illustrated in FIG. 3. In an embodiment, predetermined length 13a is 1 centimeter. Diverging portion 11a is further disclosed as having a truncated conical shape with an expanded circular cross sectional area located in downstream direction 4 from the other portion of cannula tip body 9a. Diverging portion 11a serves as an outlet for the blood flow from the blood pumping apparatus into an artery (not illustrated). Although diverging portion 11a, and diverging portions 11b and 11c in the second and third embodiments respectively, are disclosed as being conical in shape, other diverging shapes are possible. In an embodiment, for example, diverging portions 11a, 11b, and/or 11c can have a curved or flared configuration.

The expanded cross sectional area of diverging portion 11a diffuses the flow of blood and results in a decreased flow velocity of the jet or flow of blood from cannula tip 3a as well as other improved flow characteristics of the blood flow as it enters into either an artery or aorta 6. Among the improvements to the flow characteristics of the blood flow is the observed ability of the flow to maintain a laminar flow pattern for a greater distance into artery or aorta 6. This improved flow pattern in turn, is believed to reduce stress on the arterial walls of artery or aorta 6 and also a reduced likelihood of sub-lethal hemolysis blood damage as a result of fluid shear stresses around the cannula jet.

It has been established through experimentation and analysis that causing the flow of blood in cannula tip to rotate within the cannula tip provides additional advantages with regarding to the flow's ability to maintain a laminar flow profile for greater distance after it enters an artery. More specifically, the addition of a swirl inducing means within the cannula tip causes the blood flow to rotate around the longitudinal axis of the cannula tip and forestalls turbulent flow of blood for a greater distance after it has entered an artery.

Second Embodiment

It must be kept in mind that while this second embodiment and the third embodiment described below reflect the invention herein disclosed in terms of aortic insertion, this disclosure is also applicable to arterial insertion in general.

Figure 8:
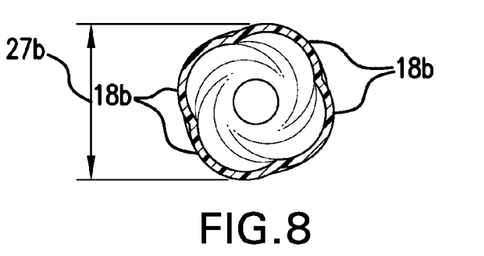
FIG. 8 illustrates a sectional view taken through section 8-8 of FIG. 6. For ease of viewing, the size of the cross section depicted in FIG. 8 is larger than it would otherwise be.
Figure 9:
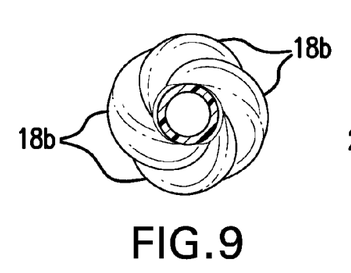
FIG. 9 illustrates a sectional view taken through section 9-9 of FIG. 6. For ease of viewing, the size of FIG. 9 is depicted as larger than it would otherwise be.
Figure 10:
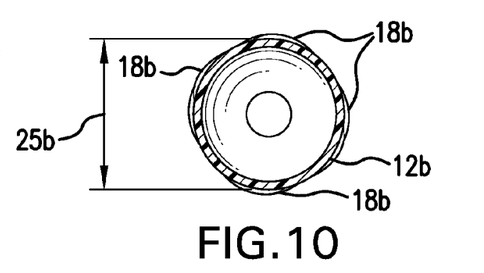
FIG. 10 illustrates a sectional view taken through section 10-10 of FIG. 6. For ease of viewing, the size of FIG. 10 is depicted as larger than it otherwise would be.

Referring now to FIGS. 6, 7, 8, 9, and 10, FIG. 6 depicts a cannula tip 3b that has cannula tip body 9b and an inlet 2b which has a first predetermined diameter 23b and a diverging portion 11b in a downstream direction 4 from inlet 2b. Diverging portion 11b has a second predetermined diameter 25b as illustrated in FIG. 10 and is further illustrated as having a predetermined length 13b as measured from throat 21b (as described below) to second predetermined diameter 25b. In an embodiment, predetermined length 13b is 1 centimeter.

Figure 6:
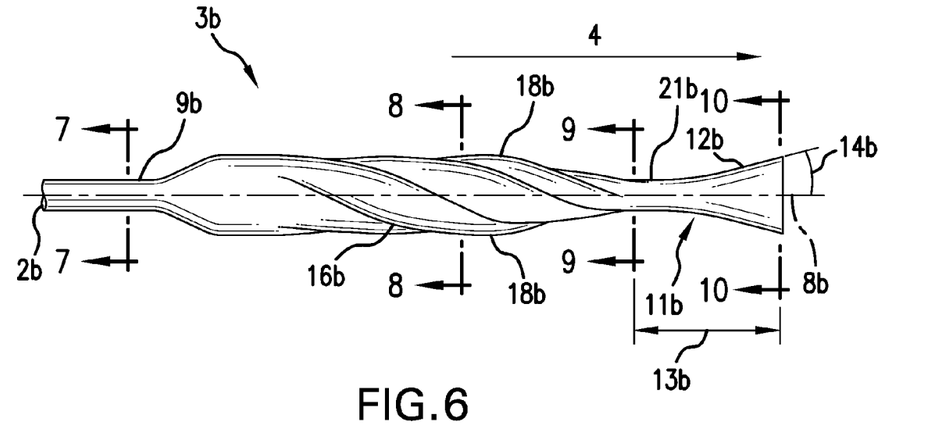
FIG. 6 illustrates an embodiment of the diverging diffuser type of outlet and a plurality of swirl inducing lobes.
Figure 7:
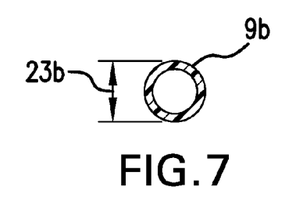
FIG. 7 illustrates a sectional view taken through section 7-7 of FIG. 6. For ease of viewing, the size of the cross section depicted in FIG. 7 is larger than it would otherwise be.

Cannula tip body 9b includes a swirl inducing portion 16b located between inlet 2b and diverging portion 11b. Swirl inducing portion 16b is illustrated as having a third predetermined diameter 27b as shown in FIG. 8 which in an embodiment is illustrated and swirl inducing portion 16b is three times the diameter of the inlet 2b and swirl inducing portion 16b has four lobes 18b oriented in a helical orientation 90 degrees apart around the longitudinal axis 8b of cannula tip 3b. In another embodiment, the swirl inducing portion 16b is at least three times the diameter of the inlet 2b. In another embodiment, the swirl inducing portion 16b is at least about three times the diameter of the inlet 2b. In another embodiment, swirl inducing portion 16b has at least four lobes 18b oriented in a helical orientation 90 degrees apart around the longitudinal axis 8b of cannula tip 3b.

The effect of lobes 18b is to impart a helical flow to the blood in cannula tip body 9b about longitudinal axis 8b. In an embodiment, the four lobes 18b are disclosed as partially convex in a radially outward direction from longitudinal axis 8b. In another embodiment, the four lobes 18b are disclosed as partially circular in a radially outward direction from longitudinal axis 8b. Each of the four lobes 18b begins at a location along cannula tip 3b in the vicinity of section 7. (In an alternate embodiment (not shown), there are at least four lobes. In another alternate embodiment (not shown), there are at least about four lobes.) Proceeding in downstream direction 4, the diameter of the swirl inducing portion 16*b* increases to a third predetermined diameter 27*b* as illustrated in FIG. 8. Still referring to FIG. 6 together with FIGS. 7, 8, 9, and 10, continuing along the longitudinal axis 8*b* in downstream direction 4, the diameter of cannula tip 3*a* decreases and the lobes 18*b* diminish until a throat 21*b* is formed as illustrated by FIG. 9. Throat 21*b* is circular in cross section and has a diameter which is approximately the same diameter as-inlet 2*b*.

Still continuing in downstream direction 4, the blood flow enters diverging portion 11*b*. In a manner similar to the first embodiment, diverging portion 11*b* is conical in shape and has a second predetermined diameter 25*b* (as illustrated in FIG. 10) located in downstream direction 4 from swirl inducing portion 16*b* as illustrated in FIG. 6. It should be noted that in an embodiment, diverging portion 11*b* can be provided with a flared configuration as noted above. Still referring to FIG. 6, diverging portion 11*b* has surface 12*b* and acts as a diffuser for the blood flow. Diverging portion 11*b* also has a predetermined length 13*b* as illustrated in FIG. 6. The surface 12*b* of diverging portion 11*b* makes an angle 14*b* with the longitudinal axis 8*b* of the cannula tip 3*b*. In an embodiment, angle 14*b* is 7 degrees. In still another embodiment, length 13*b* is 1 cm.

In-silico and in-vitro experimentation has indicated a very significant improvement in the flow characteristics of blood entering an artery in general, artery or aorta 6 in particular, as a result of the combination of swirl inducing portion 16*b* and diverging portion 11*b*. The temporal unsteadiness of the blood flow into an artery 6 is notably reduced in comparison with a standard end-hole cannula tip of similar diameter. Specifically, analysis of the blood flow has confirmed an enhanced laminar flow regime when unsteady flow was observed for conventional prior art end-hole cannulae, and the desirable laminar flow characteristics are maintained for a greater distance into that artery.

Third Embodiment

Figure 11:
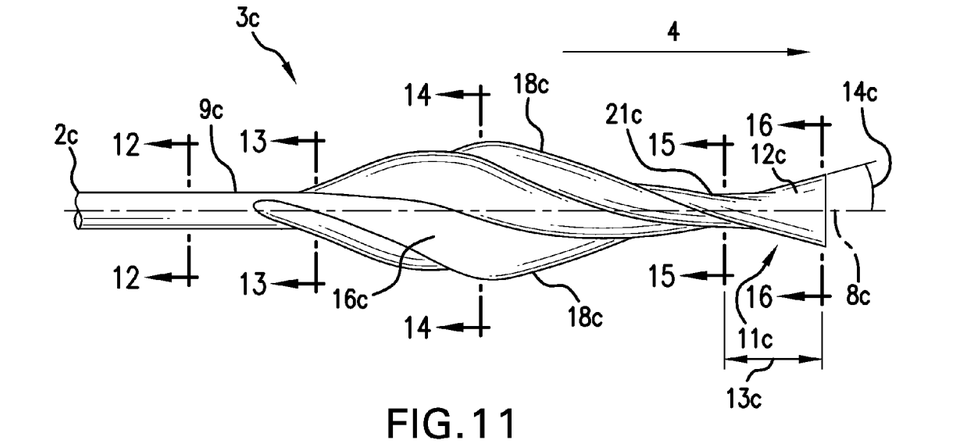
FIG. 11 illustrates an embodiment of the diverging diffuser type of outlet and a plurality of more pronounced swirl inducing lobes.
Figure 12:
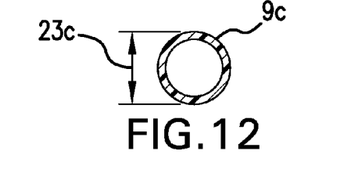
FIG. 12 illustrates a sectional view taken through section 12-12 of FIG. 11. For ease of viewing, the size of FIG. 12 is depicted as larger than it would otherwise be.
Figure 13:
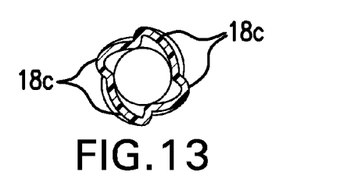
FIG. 13 illustrates a sectional view taken through section 13-13 of FIG. 11. For ease of viewing, the size of FIG. 13 is depicted as larger than it would otherwise be.
Figure 14:
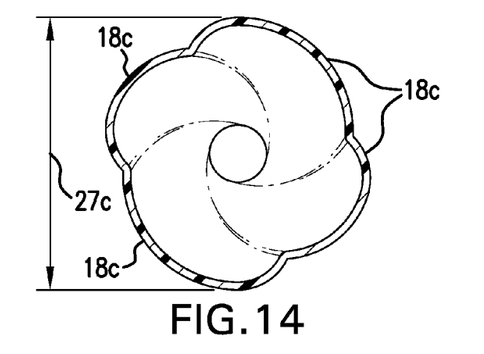
FIG. 14 illustrates a sectional view taken through section 14-14 of FIG. 11. For ease of viewing, the size of FIG. 14 is depicted as larger than it would otherwise be.

Referring now to FIG. 11 in conjunction with FIGS. 1, 12, 13, 14, 15, and 16, a larger and more pronounced swirl inducing portion 16*c* is disclosed. Inlet 2*c* of cannula tip 3*c* as shown in FIG. 11 has first predetermined diameter 23*c* (as shown in FIG. 12) and has roughly the same cross sectional area as inlet 2*b* as shown in FIG. 7 in the second embodiment. However, the third predetermined diameter 27*c* of swirl inducing portion 16*c* (as illustrated in FIG. 14) has been increased to four times the first predetermined diameter 23*c* of inlet 2*c* as may be seen in FIG. 12. In another embodiment, the third predetermined diameter 27*c* of swirl inducing portion 16*c* is at least four times the first predetermined diameter 23*c* of inlet 2*c*. In still another embodiment, the third predetermined diameter 27*c* of swirl inducing portion 16*c* is at least about four times the first predetermined diameter 23*c* of inlet 2*c*.

Figure 15:
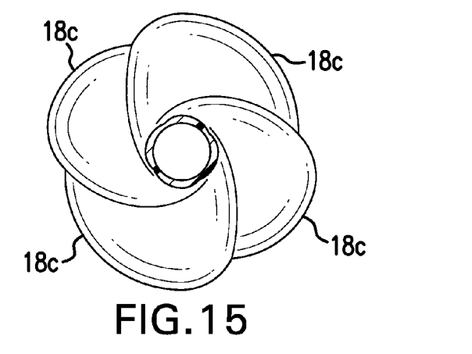
FIG. 15 illustrates a sectional view taken through section 15-15 of FIG. 11. For ease of viewing, the size of FIG. 15 is depicted as larger than it would otherwise be.
Figure 16:
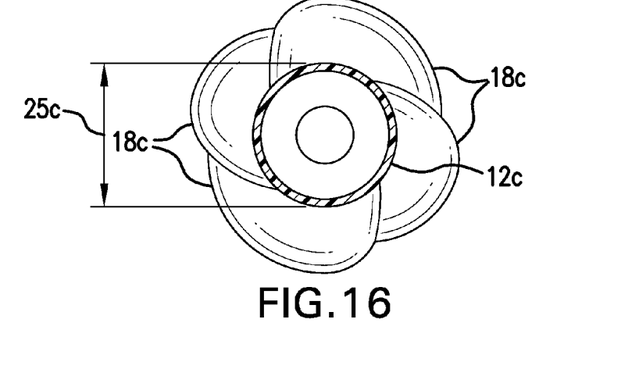
FIG. 16 illustrates a sectional view taken through section 16-16 of FIG. 11. For ease of viewing, the size of FIG. 16 is depicted as larger than it would otherwise be.

In a general embodiment, swirl inducing means includes a diverging profile followed by a converging profile. In an embodiment, swirl inducing portion 16*c* is a swirl inducing means which includes a diverging profile followed by a converging profile. The cross sectional area of throat 21*c* is shown in FIG. 15 to be approximately the same diameter as first predetermined diameter 23*c* of inlet 2*c*. As a result, the diameter of swirl inducing section 16*c* increases in downstream direction 4 from first predetermined diameter 23*c* to third predetermined diameter 27*c* and then decreases in the area of throat 21*c* to approximately the first predetermined diameter 23*c* of inlet 2*c*. This, in turn, creates a diverging profile from first predetermined diameter 23*c* of inlet 2*c* to third predetermined diameter 27*c* of swirl inducing portion 16*c*, followed by a converging profile from third predetermined diameter 27*c* to throat 21*c*. Diverging portion 11*c* has second predetermined diameter 25*c* and is further illustrated as having a predetermined length 13*c* as illustrated in FIG. 11. In an embodiment, predetermined length 13*c* is 1 centimeter. As in the first and second embodiments, diverging portion 11*c* diffuses the flow of blood thereby reducing its exit velocity, and surface 12*c* of diverging portion 11*c* makes an angle 14*c* with longitudinal axis 8*c*. In an embodiment, angle 14*c* is 7 degrees. As noted previously, embodiments of diverging portion 11*c* can be provided with either a conical or a flared configuration.

FIGS. 11, 13, and 14 disclose four lobes 18*c*, which are helically disposed about longitudinal axis 8*c* but are more pronounced and more defined than lobes 18*b* in the second embodiment. (In an alternate embodiment (not shown), the cannula tip may have a plurality of lobes comprising of at least four lobes. In another alternate embodiment (not shown), the cannula tip may have a plurality of lobes comprising of at least about four lobes.) Furthermore, lobes 18*c* encompass a 360 degree "twist" or helical rotation along longitudinal axis 8*c* of swirl inducing portion 16*c*. In another embodiment, lobes 18*c* encompass at least a 360 degree "twist" or helical rotation along longitudinal axis 8*c* of swirl inducing portion 16*c*. In another embodiment, lobes 18*c* encompass at least about a 360 degree "twist" or helical rotation along longitudinal axis 8*c* of swirl inducing portion 16*c*. This larger and more pronounced swirl inducing portion 16*c* has the effect of rotating blood flowing through cannula tip 3*c* through a greater angle than in the second embodiment, which has proven to be of greater advantage in some applications. The enhanced swirl added to the flow of blood has been demonstrated to be superior to conventional end-hole cannulae in term of flow rate versus pressure drop perfusion characteristics.

Figure 17:
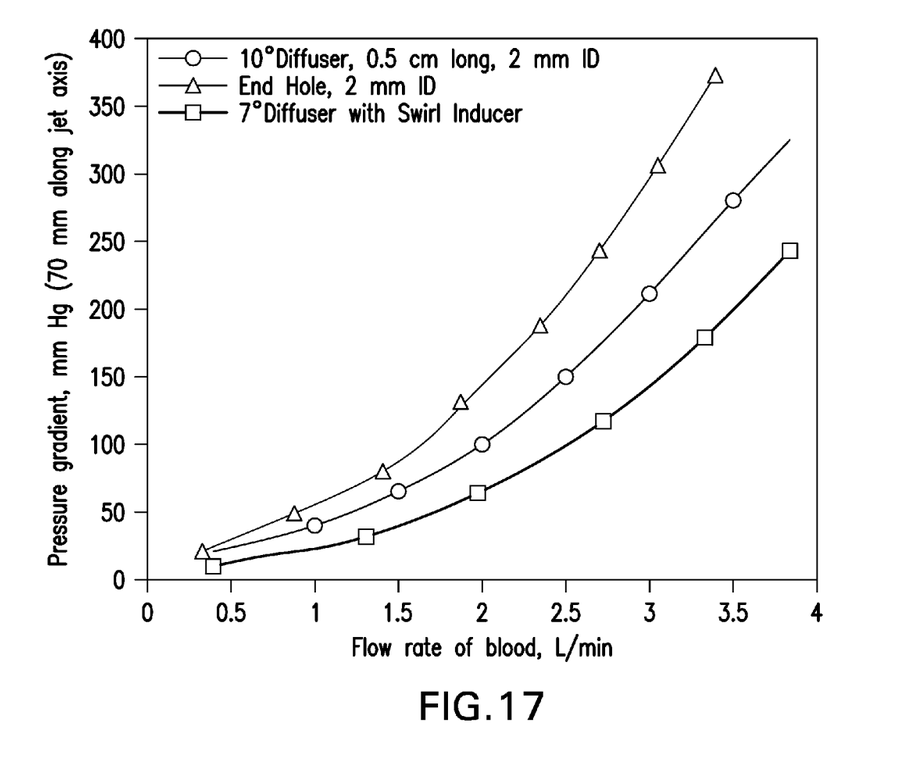
FIG. 17 illustrates a graphical depiction of pressure gradient versus flow rate across the tip of the cannula, along the axis of the cannula jet, for selected embodiments of the invention disclosed herein.

This is more particularly illustrated in FIG. 17, which is a graphical depiction of the results of an in-silico analysis studying pressure flow characteristics measured 70 mm along the blood flow jet axis (a virtual continuation of longitudinal axis 8*a* and 8*c*) for an existing prior art 2 mm end-hole cannula tip, a cannula tip configured as in the third embodiment, and a cannula tip configured as in an alternative embodiment having an angle 14*c* of 10 degrees.

Those skilled in the art will recognize that it is advantageous to have a low pressure gradient, reflected by the slope or shallowness of each of the graphs shown on FIG. 17. As may be seen from FIG. 17, the less desirable steep gradient or slope is attributed to the end-hole cannula tip while the more desirable shallow gradient is reflected by the cannula tip in the configuration of the third embodiment. Thus, it may be seen that the invention disclosed herein is able to deliver markedly improved pressure flow characteristics for blood flowing from cannula tips 3*a*, 3*b*, and 3*c* as opposed to the prior art. This in turn results in reduced pressure on arterial walls, lower turbulence of the blood flow, and reduced sub-lethal hemolysis blood damage. In-silico observations have also confirmed that cerebral perfusion improved with the use of embodiments 3*a*, 3*b*, and 3*c*.

It should also be noted that in the case of cannualization of the aorta 6, the angle of incidence of the blood flow jet has in impact on the formation of undesirable vortices and flows within aorta 6. It has been determined by in-silico studies to be beneficial to direct the blood flow jet so that it does not impinge directly upon the walls of the transverse aortic arch 7. Referring back to FIG. 1, cannula tip 3*c* and its longitudinal axis 8c are illustrated as having been oriented so as to direct the blood flow jet away from the aortic arch 7 in direction 5 toward descending aorta 10. Due to the improved cohesiveness of the blood flow jet resulting from the embodiments 3a, 3b, and 3c described herein, the blood flow jet remains in laminar flow for a greater distance and can be more successfully directed toward descending aorta 10. Furthermore, complex vertical structures are greatly reduced prior to the blood flow jet impinging on the descending aorta 10. This in turn has been observed to result in lowered hemolysis and backflow into the brachiocephalic artery.

What is claimed is:

1. A cannula tip for a cannula for conveying blood in a downstream direction into an artery, said cannula tip having an inlet having a first predetermined diameter, a longitudinal axis, a body portion, and a diverging portion having a second predetermined diameter, and wherein
said body portion includes a swirl inducing means downstream from said inlet for causing the rotation of a flow of said blood within said cannula tip around said longitudinal axis,
said swirl inducing means has a third predetermined diameter which is at least about three times said first predetermined diameter of said inlet, and
said swirl inducing means is able to cause blood flowing in said cannula tip to undergo at least about a 360 degree rotation about said longitudinal axis.

2. The cannula tip of claim 1 wherein said swirl inducing means includes a diverging profile followed by a converging profile.

3. The cannula tip of claim 1 wherein said artery is an aortic artery.

4. A cannula tip for a cannula for conveying blood in a downstream direction into an aorta, said cannula tip having an inlet portion having a first predetermined diameter, a longitudinal axis, a diverging portion serving as an outlet having a second predetermined diameter for directing a flow of blood into said aorta, a body portion situated between said inlet and said diverging portion, said body portion having a plurality of lobes disposed in a helical orientation around said longitudinal axis wherein blood flowing through said lobes undergoes a rotation of at least about 360 degrees about said longitudinal axis, said lobes having a peripheral third diameter which is at least about four times said first predetermined diameter of said inlet.

5. The cannula tip of claim 4 wherein said body portion includes swirl inducing means downstream from said inlet for causing a rotation of a flow of said blood within said cannula tip around said longitudinal axis.

* * * * *